United States Patent
Von Hoff et al.

(10) Patent No.: US 6,562,870 B1
(45) Date of Patent: May 13, 2003

(54) TREATMENT OF AIDS-ASSOCIATED NON-HODGKIN'S LYMPHOMA BY GALLIUM NITRATE

(76) Inventors: Daniel D. Von Hoff, 226 Branch Oak Way, San Antonio, TX (US) 78230; Alan A. Rubin, 207 Hitching Post Dr., Wilmington, DE (US) 19803

( * ) Notice: Subject to any disclaimer, the term of this patent is extended or adjusted under 35 U.S.C. 154(b) by 2019 days.

(21) Appl. No.: 08/527,880

(22) Filed: Sep. 14, 1995

Related U.S. Application Data

(63) Continuation-in-part of application No. 08/212,701, filed on Mar. 11, 1994.

(51) Int. Cl.⁷ ............................................... A61K 31/135
(52) U.S. Cl. ...................................................... 514/650
(58) Field of Search .......................................... 514/650

(56) References Cited

U.S. PATENT DOCUMENTS 4,529,593 A * 7/1985 Warrell et al. ............... 424/127

OTHER PUBLICATIONS

Warrell et al, 1987, Biological Abstract, vol. 83 (7), No. 67262.*
Warrell et al, 1982, Cancer vol. 51, pp 1982–87.*
Hort et al 1971, PNAS vol. 68(7), pp 1623–26.*

* cited by examiner

*Primary Examiner*—Russell Travers
(74) *Attorney, Agent, or Firm*—Gildo E. Fato

(57) ABSTRACT

The present invention comprises an improved method of treatment of AIDS-associated non-Hodgkin's lymphoma by administering gallium nitrate in a pharmaceutically acceptable vehicle.

5 Claims, No Drawings

TREATMENT OF AIDS-ASSOCIATED NON-HODGKIN'S LYMPHOMA BY GALLIUM NITRATE

This is a continuation-in-part, of application Ser. No. 08/212,701 filed Mar. 11, 1994.

BACKGROUND OF THE INVENTION

1. Field of the Invention

This invention relates to an improvement in the treatment of certain malignant lymphomas associated with acquired immunodeficiency syndrome (AIDS), and in particular, non-Hodgkin's lymphoma (NHL). More specifically, the present invention is directed to the therapeutic use of gallium nitrate in AIDS-associated NHL.

2. Background and Prior Art

NHL is one of the most common malignancies associated with human immunodeficiency virus (HIV) infection. AIDS-associated NHL is typically an aggressive B-cell lymphoma, often extra nodal, that affects the gastrointestinal tract, central nervous system, bone marrow and liver. Response to chemotherapy is poor and the mortality rate high.

The occurrence of NHL in HIV-infected individuals has increased dramatically since the onset of the AIDS epidemic. Projections of AIDS-associated NHL incidence based on the National Cancer Institute's program of Surveillance, Epidemiology and End Results (SEER) suggest that between 2900 (8%) and 9800 (27%) of all NHL cases that occurred in the US in 1992 are related to HIV infection (Gall, M. H. et al., *J. Natl. Cancer Inst.*, 83:695, 1991). NHL incidence has been found to increase exponentially with increasing duration of HIV infection. Accordingly, improvements in AIDS therapy that prolong survival may result in even more AIDS-associated NHL than predicted from current epidemiologic studies.

Treatment of AIDS-associated NHL has relied primarily upon drug combinations previously found to be effective in HIV(-)NHL. Some examples of these regimens include the: following: CHOP (cyclophosphamide, doxorubicin, vincristine, prednisone); M-BACOD (methotrexate, bleomycin, doxorubicin, cyclophospharmide, vincristine, dexamethasone); PROMACE-MOPP (prednisone, methotrexate, doxorubicin, cyclophosphamide, epipodophyllotoxin administered in alternating cycles with nitrogen mustard, vincristine, procarbazine, prednisone); and COMET-A (cyclophosphamide, vincristine, methotrexate with leucovorin calcium rescue, etoposide, cytarabine).

Despite this variety of treatment regimens, response rates have been poor. There is clearly no consensus on the beset NHL treatment for AIDS patients and new approaches are avidly sought (Ziegler, J. L. et al., *N. Engl. J. Med.*, 311:565, 1984; Kaplan, L. D. et al., *JAMA*, 261:719, 1989). A major drawback of all NHL combination chemotherapies is their tendency to exacerbate the underlying immunodeficiency of AIDS. Current therapeutic efforts are aimed at preventing the myelosuppression and immunosuppression associated with these regiments (Pluda, J. M. et al., *Ann. Oncol., Supp* 2:191, 1991).

The strategy proposed in the present invention is to use gallium nitrate, either alone or in combination with other chemotherapeutic agents, to treat AIDS-associated NHL. Gallium nitrate has already been found to be well tolerated and effective in treating HIV negative patients with advanced NHL (Welck, J. K. et al., *Cancer Treat. Rep.*, 67:823, 1983; Warrell, R. P. et al., *Cancer*, 51:7982, 1983). More importantly, gallium nitrate causes little or no myelosuppression or immunosuppression, and therefore represents a highly rational and appropriate treatment modality for AIDS-associated NHL. In addition, gallium nitrate crosses the blood-brain barrier which will allow treatment of the central nervous system lymphoma often seen in patients with AIDS-associated lymphoma.

The earliest published observations of gallium's anticancer effects in patients were made more than 40 years ago by King et al., (*Arch. Int. Med.*, 90:785, 1952) for the radioactive form of this Group IIIa element. Almost 20 years later, nonradioactive gallium salts were also reported to cause tumor regression by Hart et al. (*Proc. Nat. Acad. Sci.*, 68:1623, 1971). More recently, U.S. Pat. No. 4,529,593 (1985) and U.S. Pat. No. 4,704,277 (1987) disclose methods of treating disorders of calcium homeostasis with gallium salts, including those disorders caused by direct invasion of bone by malignant tumors.

SUMMARY OF THE INVENTION

It is the purpose and principal object of the present invention to provide an improved method for the treatment of AIDS-associated NHL by using a chemotherapeutic agent, gallium nitrate, which (a) is effective against NHL and yet which (b) does not accentuate certain debilitating effects in AIDS patients, such as myelosuppression and immunosuppression, commonly exacerbated by other anti-NHL agents.

DETAILED DESCRIPTION

In the method of the present invention, gallium nitrate may be administered orally or parenterally in amounts from 100–400 mg/sq m/day. The preferred route of administration is by injection. In its injectable form, gallium nitrate is a clear solution containing the hydrated nitrate salt of the group IIIa element, gallium. The compound is formed by the reaction of elemental gallium with nitric acid, followed by crystallization of gallium nitrate from solution. The stable nonanhydrate is a white, slightly hygroscopic, crystalline powder of molecular weight 417.87 that is readily soluble in water.

The preferred dose of gallium nitrate is 300 mg/sq m/day for 7 days administered as an intravenous solution. Each ml contains 25 mg of gallium nitrate (on an anhydrate basis), sodium citrate dihydrate and sodium hydroxide for pH adjustment to 6.0–7.0. The daily dose is diluted in 1000 cc of 0.9% Sodium Chloride Injection, USP, or 5% Dextrose Injection, USP, for infusion over 24 hours. Both solutions are stable for 48 hours at room temperature (15–30° C.) and for 7 days if stored under refrigeration (2–8° C.). Courses of gallium nitrate are given every 3 weeks to patients with pathologically verifiable diagnosis of AIDS-associated NHL. Supportive care medications including antiretroviral, antipneumocystis, antifungal and other relevant AIDS or AIDS-related therapies may be given concurrently with gallium nitrate.

The following experiments were performed to ascertain gallium nitrate's effect in vitro in rapidly dividing cell lines and in a patient with AIDS-associated NHL.

EXAMPLE 1

Effect of Gallium Nitrate in Vitro

In tissue culture experiments, gallium nitrate is cytotoxic against AS283 and Raji line lymphoblast-like cells. Both human tumor cell lines were maintained in RPMI 1640 medium plus 10% fetal calf serum. They were seeded in 15-ml rubber-stoppered vials containing 2 $\mu$Ci of ($^{14}$C) glucose and 2 ml of tissue culture media. Gallium nitrate or control vehicle was added to the vials, the vials were flushed with a mixture of 5% $CO_2$ plus air and then incubated at 37° C. On days 6, 9 and 12, the vials were removed from the incubator and evaluated radiometrically for the amount of $^{14}CO_2$ produced. Inhibition of conversion of ($^{14}$C) glucose to $^{14}CO_2$ is a reliable index of cytotoxicity (Von Hoff et al., Cancer Res. 45:4032–4038, 1985). The cytotoxic effects of gallium nitrate, expressed as per cent survival of the tumor cells, are shown in Table 1.

TABLE 1

| TREATMENT | FINAL CONCENTRATION (mcg/ml) | % SURVIVAL | |
|---|---|---|---|
| | | RAJI | AS283 |
| Control | — | 100 | 100 |
| Gallium Nitrate | 100 | 33 | 0 |
| Gallium Nitrate | 50 | — | 58 |
| Gallium Nitrate | 10 | 114 | 122 |
| Gallium Nitrate | 1 | 102 | 99 |

EXAMPLE 2

Clinical Study

In a clinical trial designed to evaluate the effects of gallium nitrate on AIDS-associated NHL, the first patient entered has responded favorably to treatment. The patient, a 35-year old Hispanic female, had been essentially unresponsive to previous treatment with CHOP, mitoguazone and the combination cyclophosphamide+doxorubicin+etoposide. She had developed a 9.0×9.0 cm infraclavicular node that was palpable on physical examination and a smaller 3.0×2.0 cm node within her right axilla. The nodes decreased in size following treatment with gallium nitrate (300 mg/sq m/day for 7 days) administered by intravenous infusion every 24 hours. After a second course of treatment three weeks later, the infraclavicular node was not palpable at all and the axillary node was reduced to 2.0×1.5 cm. This excellent peripheral response was not accompanied by apparent drug-related adverse effects, and holds promise for gallium nitrate therapy in AIDS-associated NHL.

What is claimed is:

1. A method for treating AIDS-associated non-Hodgkin's lymphoma (NHL) in a human immunodeficiency virus (HIV) positive human individual, such treatment comprising administering to the individual an effective amount of pharmaceutically acceptable gallium nitrate.

2. Method of claim 1 wherein gallium nitrate is administered parenterally in amounts ranging from 100–400 mg/sq m/day either alone or in combination with other chemotherapeutic agents.

3. Method of claim 2 wherein the gallium nitrate is administered intravenously.

4. A method for treating AIDS-associated non-Hodgkin's lymphoma (NHL) in a human immunodeficiency virus (HIV) positive human individual, such treatment comprising administering to the individual an effective amount of pharmaceutically acceptable gallium salt.

5. Method of claim 4 wherein gallium salt is administered parenterally in amounts ranging from 100–400 mg/sq m/day either alone or in combination with other chemotherapeutic agents.

* * * * *